Figure 1:
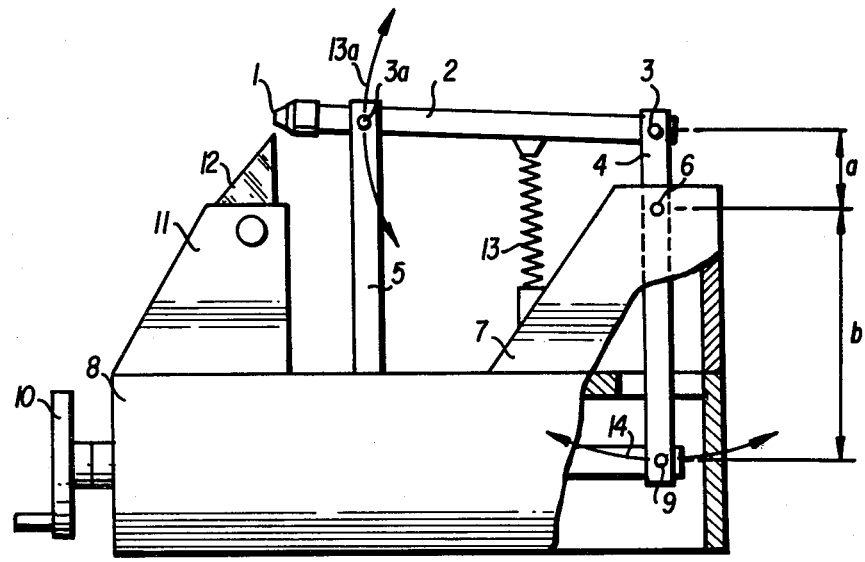

United States Patent [19]

Sitte et al.

[11] 4,221,438

[45] Sep. 9, 1980

[54] BEARING SYSTEM FOR THE PIVOT BAR OF MICROTOMES PARTICULARLY ULTRAMICROTOMES

[75] Inventors: Hellmuth Sitte, Seefeld; Heinrich Kleber, Vienna, both of Austria

[73] Assignee: C. Reichert Optische Werke, AG, Vienna, Austria

[21] Appl. No.: 945,371

[22] Filed: Sep. 25, 1978

[51] Int. Cl.³ .................... F16C 11/06; F16C 11/12
[52] U.S. Cl. .................... 308/2 R; 308/189 R
[58] Field of Search ............ 29/149.5 B; 308/2 R, 308/21, 72, 189 R

[56] References Cited

U.S. PATENT DOCUMENTS

| 2,375,322 | 5/1945 | Pierce | 308/2 R |
|---|---|---|---|
| 3,220,524 | 1/1965 | Puidokas | 308/2 R X |
| 3,667,789 | 6/1972 | McNeely et al. | 29/149.5 B |

FOREIGN PATENT DOCUMENTS 238963 7/1963 Austria .

Primary Examiner—Frederick R. Schmidt
Attorney, Agent, or Firm—Jeremiah J. Duggan; Alan H. Spencer; Stephen A. Schneeberger

[57] ABSTRACT

A joint having a plurality of spherical elements cemented to one member and the other member having adjustable sockets which cooperate with the spherical elements to permit rotation about a single axis. The joint is particularly useful in microtomes and ultramicrotomes.

7 Claims, 5 Drawing Figures

BEARING SYSTEM FOR THE PIVOT BAR OF MICROTOMES PARTICULARLY ULTRAMICROTOMES

The invention concerns a bearing system for the pivot bar of microtomes, particularly ultramicrotomes, with two bearing components which are positively connected together in each case by balls fastened to one bearing component and interlocking in appropriate bearing sockets on the other bearing component.

In the preparation of very thin sections with ultramicrotomes, the object may not be lead in the same path downwards (equals cutting stroke) and upwards (equals return stroke), since known phenomena result in the case of a specimen sliding back across the knife edge, which make impossible the preparation of a series of slices in an uninterrupted sequence. This phenomenon can be eliminated by two different methods.

On the one hand, the bearing joint for the specimen holding bar can be formed in a known way as a universal joint in such a way that the specimen holding bar can be swiveled in any direction, but not rotated around its longitudinal axis. A bearing system formed in this way makes it possible, in combination with the appropriate parts of the microtome mechanism, to lead the specimen downwards across the knife edge in the course of the cutting stroke, whereby the slice is formed, and to rotate it afterwards out of the pivot plane of the specimen holding bar in the cutting stroke, and to move it laterally from the knife in the course of the return stroke, back upwards into the starting position above the knife edge. On the other hand, it is possible to form the bearing joint of the specimen holding bar simply in the form of a hinge joint, and to prevent the sliding of the specimen in the return stroke by removing it from the knife in the pivot plane of the specimen holding bar. For this, for example, the knife or the specimen can be pulled back by a certain amount (e.g. 50 μm) magnetically or by magnetostriction during the return stroke. A specimen withdrawal can also be effected by a controlled motion of the bearing, for example, by means of a cam plate of the microtome mechanism.

Microtomes constructed according to the construction principles explained above are called wobble bar microtomes or pivot bar microtomes.

In both cases, the bearing components of the bearing system must be moved so precisely and reproducibly with consideration of the minimal slice thicknesses to be obtained, that interfering irregularities of the bearing function can be excluded with certainty. In addition, the bearing components should be built sturdy enough so that they can accept the forces necessary for the clamping of the specimen to the specimen holder bar or of the knife to the knife holder, without damage, even in case of frequent repetition of these clamping procedures, but they should nevertheless be simple to prepare and need no maintenance for a long period of time.

In pivot bar ultramicrotomes, a bearing system is needed which allows only one degree of freedom of rotation to the specimen holder bar, and reproducibly blocks the other degrees of freedom of rotation as well as all freedoms of translation. In a known bearing system of the initially described type (Austrian Pat. No. 238,963), for example, this is obtained by two balls which are supported differently. In this case, for example, one ball can be supported in a ring-shaped bearing recess, and the second in a bearing recess formed as a groove or a v-notch. In this way it is indeed possible to limit the number of degrees of freedom to one degree of rotation, without precise adjustment of the separation of the two balls, by a simple means. However, as a result of the asymmetric construction, either the bearing system is unstable or it requires relatively strong spring forces for stabilization, which leads to lubrication problems in view of the simply pointor line-shaped support of the one ball in the associated bearing recess.

It is, therefore, the purpose of the present invention to realize a bearing system of the initially described type, which does not have the defects mentioned above, and nevertheless, flexibly and positively joins the two bearing components together with one another with close tolerance, in a simple manner, so that they can be rotated only around one axis of rotation with respect to one another, and on the other hand have no freedom of translation at all.

This objective is attained according to the invention, by providing that each of the bearing sockets for the balls is formed as a spherical cup, and one of the bearing sockets or of the balls is at least transiently adjustable in the direction of the pivot axis running through the center points of the balls, for precise matching of the separation of the bearing sockets from one another to the separation of the balls, or of the balls separation to the separation of the bearing sockets.

A completely stable support of the pivot bar is provided by the design of a spherical cup in each case as the bearing socket for the balls, which is resistant to forces exerted from all directions, and as a result has a considerably greater stability of the pivot arm than is permitted by the bearing system according to the state of the art. However, since it is extraordinarily difficult with ordinary measures, even if it is not completely excluded in practice, to harmonize the mutual separations of the balls and of the ball sockets as precisely as is required for the preparation of the thinnest slices, it is furthermore provided, according to the invention, to have one of the balls or one of the bearing sockets adjustable in the direction of the pivot axis of the pivot bar, in such a way that the exact positioning of the ball or of the bearing socket is accomplished automatically in the positively joined state of the two bearing components.

Various possibilities exist for this purpose within the scope of the invention: one of the two bearing components of the bearing system jointed together flexibly can have the bearing sockets formed as spherical cups for the balls, which are fastened to the other bearing component. In this case, the separation of the two bearing sockets is exactly matched to the separation of the balls by providing that one of the four elements—one ball or one bearing socket is firmly cemented to the corresponding bearing component only in the course of the final assembly, so that it becomes exactly matched in the assembly process to the position of the corresponding contact surface. Since, according to a further improvement of the invention, the two flexibly joined bearing components are positively joined together with one another in a known way by at least one tension spring oriented symmetrically with respect to the balls, the element still not definitively fixed in position in the assembly process is oriented most precisely by the forceable tightening with the use of the still existing pliability of the adhesive. The definitive fixing of the location of this element into the exact position that it occupies takes place automatically after a short time by hardening of the adhesive.

Another embodiment of the bearing system according to the invention provides that the adjustable bearing socket or ball is formed or positioned in an element, which is held to the associated bearing component by a stiff leaf spring, and that the pivot axis of the pivot bar running through the center points of the balls, intersects perpendicularly the plane in which the leaf spring lies. The leaf spring is formed in such a way that it displays a definite flexibility only in the direction of the pivot axis of the pivot bar, i.e. in the direction in which the adjustment motion is desired. In all other directions, particularly in the plane of the leaf spring itself, however, practically no deformations appear. As a result of the pliability of the leaf spring present in the direction of the pivot axis, the element held by it, which carries the bearing socket or the ball, is adjustable to the desired extent, which is necessary for the exact matching of the separation of the bearing sockets to the separation of the balls.

A combination of the two embodiments described above also lines within the scope of the invention.

Figure 2A:
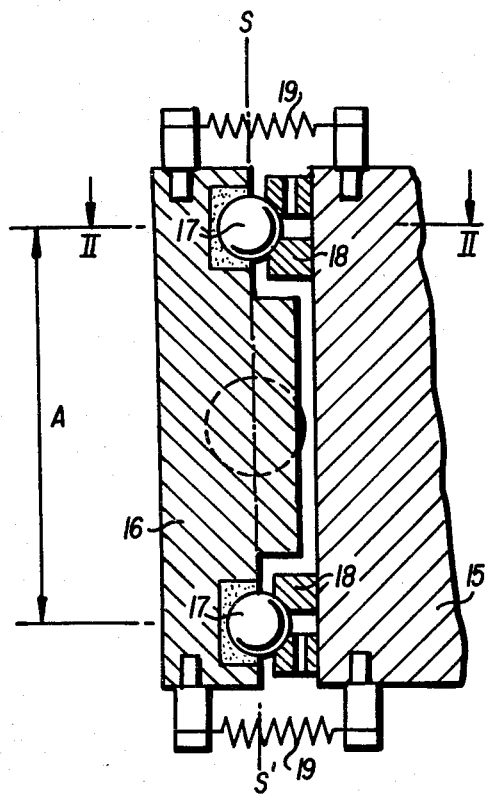
Figure 2B:
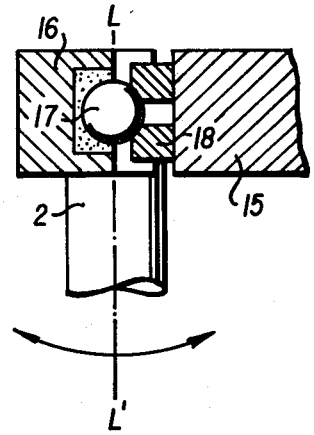

Further advantages and characteristics of the invention are apparent from the following description of preferred embodiments, with the use of the attached drawings, as well as from further sub-claims. The drawings show:

FIG. 1. A schematic side view of a pivot bar microtome;

FIG. 2a. A section along the pivot axis of a first embodiment of a bearing system according to the invention;

FIG. 2b. A section along the line II—II in FIG. 2a, and

Figure 3A:
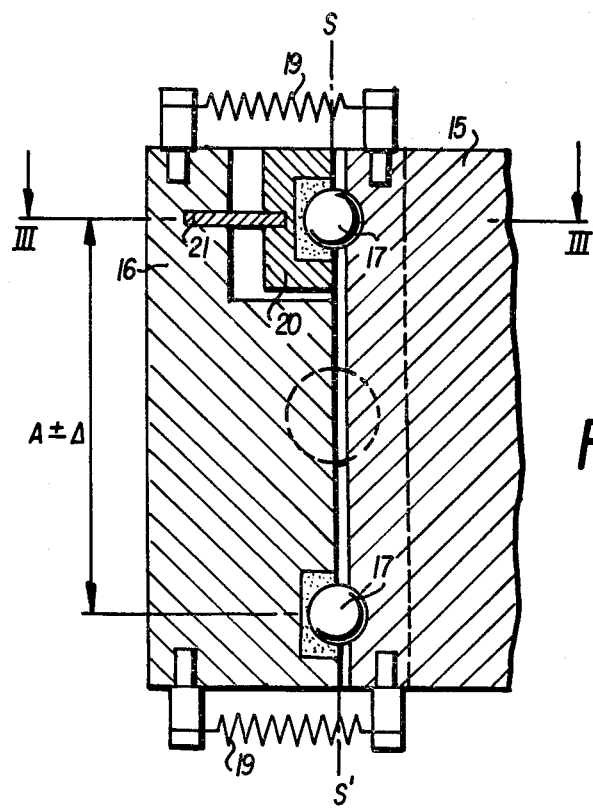

FIG. 3a, b. An illustration of a variety of embodiment analogous to FIGS. 2a, b, of the bearing system according to the invention.

The construction of the ultramicrotome shown in FIG. 1 is of the usual kind: a specimen 1 is fixed in location on a specimen holding bar 2 (pivot bar), which is flexibly connected at one end by a bearing designated as a whole by 3, with a lever 4, and at its other end at 3a, with a lever 5. The lever 4, in turn, can be supported with a joint 6 in an attachment 7 of the stand support 8, and can be flexibly joined by 9 with a suitable element of the microtome mechanism (for example, micrometer spindle, cam plate, or the like), directly or indirectly. By rotation of a hand wheel 10, the microtome mechanism installed in the base, not to be explained in more detail, in known manner brings about an upward and downward motion of the lever 5 and with it a pivoting of the specimen holding bar together with the specimen 1, in the direction of the double arrow 13a. In addition, the pivot 9 of the lever 4 can be moved in known manner by the microtome mechanism, for example, in the advanced direction designated by the double arrow 14. This motion of the pivot 9 leads to a pivoting of the lever 4 around the bearing 6 and thereby brings about an advance of the specimen holder bar 2, geared down in the ratio of the distances a/b indicated in FIG. 1, and with it of the specimen 1 fastened to it, against a knife 12 fastened in a knife holder 11, as is necessary for the preparation of slices. To obtain particularly high precision, all bearings and joints are kept free of play by spring tensions, such as, for example, a spring 13.

Figure 3B:
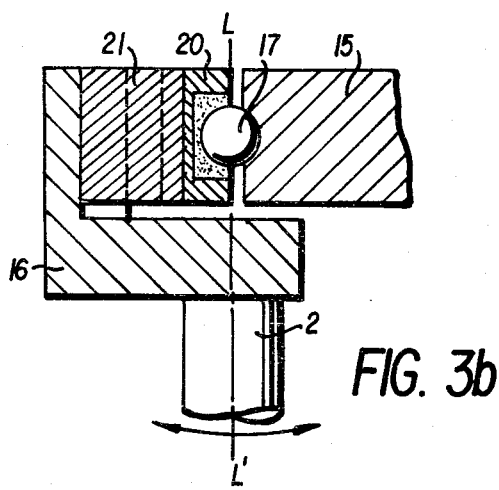

FIGS. 2 and 3 show two possible embodiments of the bearing system according to the invention, which can be realized in the bearings 3 and/or 6 according to FIG. 1.

The bearing system according to FIG. 2 consists of two bearing components 15 and 16, which are flexibly joined together with one another through two balls 17 and two cup-shaped sockets, which are formed in elements 18. In this, the balls 17 are cemented into the bearing components 16, while the elements 18, which carry the bearing sockets, are cemented to part 15. The positive joining of the two bearing components 15, 16 through the balls 17 and the elements 18 carrying the bearing sockets, is effected in known manner by symmetrically oriented tension springs 19. The specimen holding bar 2 is fastened rigidly to the bearing component 16. Its longitudinal axis LL' intersects the pivot axis SS' of the bearing system, running through the centers of the two balls. An exact agreement of the distances A of the corresponding bearing elements 17 and 18 is obtained by providing that one of the four cemented joints between the bearing element 15 and the elements 18, or the bearing element 16 and the balls 17, is formed as the last step of assembly, after all other cemented joints have already been completed and the adhesive is hardened. Until the hardening of the final adhesive joint, the entire bearing system remains in positive contact—for example with the help of the tension spring 19.

In the embodiment form of the bearing system according to the invention in accordance with FIG. 3, in contrast to the bearing system in accordance with FIG. 2, the cup-shaped bearing sockets for the balls 17 are already contained in the bearing component 15 as recesses, and show no central hole and ventilation hole, as is recognizable from the schematic illustration of FIG. 2. For correction of deviations $\pm \Delta$ from the prescribed distance A brought about by manufacturing, the one ball 17 is cemented into its own holding element 20, which is connected with the bearing element 16 through a stiff leaf spring 21. The flexibility of the leaf spring 21 permits in fact a matching of the separation of the balls 17 to the separation $A \pm \Delta$ of the corresponding bearing sockets of the bearing component 15, because of the arrangement apparent from the drawing, but because of its stiffness, prevents translations in both other directions, particularly in the advance direction.

More effectively, the cup surfaces of the bearing sockets are ground to accept the balls 17 by the process customary for the preparation of optical glass lenses, or are manufactured by the replication process from synthetic resin. The particular advantage of this development consists in that this process guarantees on the one hand an exact, interferometrically controllable spherical cavity form of the contact surfaces of the bearing sockets, and on the other hand, permits the preparation of large bearing surfaces above 10 mm$^2$, which reduce the support pressure even with spring forces above 5 kp to such and extend that a sufficient lubrication is guaranteed in long time operation. In particular, "stick slip" phenomena are prevented in this way, which appear particularly easily at the angular velocity in the range between 0.02 and 1.0 angular degrees per second required in the bearing elements in the operation of ultramicrotomes, and in view of the high precision required in the nm-range, interfere sensibly. While only bearing surfaces up to a maximum of 10 mm$^2$ for balls with diameters of approximately 10 mm can be prepared by driving or pressing steel balls into metal supports of softer metal, optical grinding and also the replication process permit the preparation of bearing surfaces above 10 mm$^2$ with the same ball diameter, and therewith permit the reduction of the bearing pressure to 1/10 or the increase of the spring forces of the tension spring 19 by ten fold, with the same lubrication conditions.

The bearing elements according to the invention can be realized in equivalent modified form—for example, by combination of the embodiments according to FIGS. 2 and 3 and of the described process for the preparation of the ball bearing surfaces—and can be used for various purposes in the construction of an ultra-microtome. Thus, the bearing system according to the invention can be used for the bearings of the specimen holder rod 2, the withdrawal device, the reduction of the advance, etc. Furthermore, the bearing elements, particularly the bearing sockets and the balls, can be prepared from various materials. Among them can be mentioned hard metals, sintered materials, suitable minerals, such as ruby or the like. Also, plastics, for example, self-lubricating synthetic resins or those treated with molybdenum disulfide, can be used.

It is also to be understood, that instead of the balls shown in the preceding examples of embodiment, bearing elements can also be used which are spherically formed only in the area of their contact surfaces.

What is claimed is:

1. Bearing system for the pivot bar of microtomes, particularly ultramicrotomes with two bearing components 15 and 16, which are positively coupled together in each case by balls fastened to one bearing component and interlocking in appropriate bearing sockets on the other bearing component, characterized in that each of the bearing sockets for the balls (17) is formed as a spherical cup, and that means are provided for the transient adjustability of one of the bearing sockets or one of the balls (17) relative to bearing components 15 and 16 in the direction of the pivot axis (SS') of the pivot bar (2) running through the center points of the balls, for exact matching of the separation $(A\pm\Delta)$ of the bearing sockets from one another to the separation of the balls (A), or of the ball separation to the separation to the separation of the bearing sockets by final assembly of the bearing system.

2. Bearing system according to claim 1, characterized in that the two joined bearing components (15, 16) are positively coupled in a known manner by at least one tension spring (19) oriented symmetrically with respect to the balls (17).

3. Bearing system according to claim 2, characterized in that the adjustable bearing socket or ball is fixed in position by a curable adhesive still in pliable condition during the assembly of the bearing components (15, 16).

4. Bearing system according to claim 1 or 2, characterized in that the adjustable bearing socket or ball is formed or set in an element (20), which is held to the associated bearing component (15, 16) by a stiff leaf spring (21), and that the pivot axis (SS') running through the center points of the balls, passes perpendicularly through the plane in which the leaf spring (21) lies.

5. Bearing system according to one of the claims 1 to 3, characterized in that the bearing sockets are precision ground by processes customary for optical lenses.

6. Bearing system according to one of the claims 1 to 3, characterized in that the contact surfaces of the balls and of the bearing sockets are formed of hardened or naturally hard, dense, sintered, or porous metals or minerals, and/or are provided with a specially prepared surface.

7. Bearing system according to one of the claims 1 to 3, characterized in that the contact surfaces of the bearing sockets are formed of casting resin and are manufactured by the replica method.

* * * * *